(12) United States Patent
Libraty (10) Patent No.: US 11,793,873 B2
(45) Date of Patent: Oct. 24, 2023

(54) BIVALENT DENGUE/HEPATITIS B VACCINES

(71) Applicant: UNIVERSITY OF MASSACHUSETTS, Boston, MA (US)

(72) Inventor: Daniel H. Libraty, Newton, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 142 days.

(21) Appl. No.: 16/612,152

(22) PCT Filed: May 1, 2018

(86) PCT No.: PCT/US2018/030542
§ 371 (c)(1),
(2) Date: Nov. 8, 2019

(87) PCT Pub. No.: WO2018/208547
PCT Pub. Date: Nov. 15, 2018

(65) Prior Publication Data
US 2021/0379182 A1    Dec. 9, 2021

Related U.S. Application Data (60) Provisional application No. 62/504,188, filed on May 10, 2017.

(51) Int. Cl.
*A61K 39/00*    (2006.01)
*A61K 39/295*    (2006.01)
(Continued)

(52) U.S. Cl.
CPC ............ *A61K 39/295* (2013.01); *A61K 39/12* (2013.01); *A61K 39/292* (2013.01); *A61K 47/65* (2017.08); *A61P 31/14* (2018.01); *A61P 31/20* (2018.01)

(58) Field of Classification Search
None
See application file for complete search history.

(56) References Cited

U.S. PATENT DOCUMENTS 5,705,188 A    1/1998    Junichi et al. ................. 424/450
7,943,148 B1 *    5/2011    Sagripanti ........ G01N 33/56983
                                                                                              424/218.1
(Continued)

FOREIGN PATENT DOCUMENTS

WO    WO 2007035530      3/2007
WO    WO-2007035530 A2 *    3/2007   ......... C07K 14/005
(Continued)

OTHER PUBLICATIONS

Chen et al., "Fusion Protein Linkers: Property, Design and Functionality," Adv Drug Deliv Rev 65(10): 1357-1369 (Year: 2013).*
(Continued)

*Primary Examiner* — M Franco G Salvoza
(74) *Attorney, Agent, or Firm* — Medlen & Carroll, LLP (57) ABSTRACT

The present invention relates to the construction of, and immunization with viral vaccines. In particular, bivalent vaccines that are capable of providing simultaneous virus infection protection for two or more different viruses. Furthermore, the bivalent vaccines contemplated herein are contemplated as being effective in a neonatal mammal. One such bivalent viral vaccine comprises two antigenic epitopes against the dengue viruses and at least one antigenic epitope against hepatitis B virus. Immunization cross-reactivity may also provide infection protection against other viruses as well.

14 Claims, 6 Drawing Sheets
Specification includes a Sequence Listing.

(51) Int. Cl.
*A61K 47/65* (2017.01)
*A61P 31/20* (2006.01)
*A61P 31/14* (2006.01)
*A61K 39/12* (2006.01)
*A61K 39/29* (2006.01)

(56) References Cited

U.S. PATENT DOCUMENTS

| | | | |
|---|---|---|---|
| 2012/0321659 A1 | 12/2012 | Murray | 424/196.11 |
| 2013/0064843 A1 | 3/2013 | Brusic et al. | 424/186.1 |
| 2013/0202634 A1* | 8/2013 | Shresta | C12N 7/00 530/328 |
| 2013/0287857 A1 | 10/2013 | von Andrian et al. | 424/501 |
| 2015/0174237 A1 | 6/2015 | Mond et al. | 424/186.1 |
| 2015/0265694 A1* | 9/2015 | Isern | A61P 31/14 530/350 |
| 2016/0251413 A1 | 9/2016 | Robinson et al. | 424/159.1 |
| 2018/0050084 A1* | 2/2018 | Williams, III | A61P 11/06 |
| 2019/0300580 A1* | 10/2019 | Laing | G01N 33/56983 |

FOREIGN PATENT DOCUMENTS

| | | |
|---|---|---|
| WO | WO 2015175361 | 11/2015 |
| WO | WO 2016/034974 | 3/2016 |
| WO | WO 2017/070624 | 4/2017 |
| WO | WO 2017/070624 A | 4/2017 |
| WO | WO 2017/070624 B | 4/2017 |
| WO | WO 2017/070624 C | 4/2017 |
| WO | WO 2018/037365 | 3/2018 |

OTHER PUBLICATIONS

Gregory et al., "Structure and function of the complete internal fusion loop from Ebolavirus glycoprotein 2," PNAS, vol. 108, No. 27 11211-11216 (Year: 2011).*

An, et al., "Preparation and Testing of a Haemophilus Influenzae Type B/Hepatitis B Surface Antigen Conjugate Vaccine." *Vaccine*, 33(13):1614-1619 (2015).

Bhatt, et al., "The Global Distribution and Burden of Dengue." *Nature*, 496(7446):504-507 (2013).

Brewoo, et al., "Immunogenicity and Efficacy of Chimeric Dengue Vaccine (Denvax) Formulations in Interferon-Deficient Ag129 Mice." *Vaccine*, 30(8):1513-1520 (2012).

Capeding, et al., "Clinical Efficacy and Safety of a Novel Tetravalent Dengue Vaccine in Healthy Children in Asia: A Phase 3, Randomised, Observer-Masked, Placebo-Controlled Trial." *Lancet*, 384(9951):1358-1365 (2014).

Costin, et al., "Mechanistic Study of Broadly Neutralizing Human Monoclonal Antibodies against Dengue Virus That Target the Fusion Loop." *J Virol*, 87(1):52-66 (2013).

de Alwisde Silva, "Measuring Antibody Neutralization of Dengue Virus (Denv) Using a Flow Cytometry-Based Technique." *Methods Mol Biol*, 1138:27-39 (2014).

Diamond, et al., "Infection of Human Cells by Dengue Virus Is Modulated by Different Cell Types and Viral Strains." *J Virol*, 74(17):7814-7823 (2000).

Henchai and Putnak, "The Dengue Viruses." *Clin Microbiol Rev*, 3(4):376-396 (1990).

Kraus, et al., "Comparison of Plaque- and Flow Cytometry-Based Methods for Measuring Dengue Virus Neutralization."*J Clin Microbiol*, 45(11):3777-3780 (2007).

Littaua, et al., "Human IgG Fc Receptor II Mediates Antibody-Dependent Enhancement of Dengue Virus Infection." *J Immunol*, 144(8):3183-3186 (1990).

Puerta-Guardo, et al., "Antibody-Dependent Enhancement of Dengue Virus Infection in U937 Cells Requires Cholesterol-Rich Membrane Microdomains." *J Gen Virol*, 91(Pt 2):394-403 (2010).

Sabchareon, et al., "Protective Efficacy of the Recombinant, Live-Attenuated, Cyd Tetravalent Dengue Vaccine in Thai Schoolchildren: A Randomised, Controlled Phase 2b Trial." *Lancet*, 380(9853):1559-1567 (2012).

Shouval, et al., "Improved Immunogenicity in Mice of a Mammalian Cell-Derived Recombinant Hepatitis B Vaccine Containing Pre-S1 and Pre-S2 Antigens as Compared with Conventional Yeast-Derived Vaccines." *Vaccine*, 12(15):1453-1459 (1994).

Simmons, et al., "Antibody Prophylaxis against Dengue Virus 2 Infection in Non-Human Primates." *Am J Trap Med Hyg*, 95(5):1148-1156 (2016).

Smith, et al., "The Potent and Broadly Neutralizing Human Dengue Virus-Specific Monoclonal Antibody 1c19 Reveals a Unique Cross-Reactive Epitope on the BC Loop of Domain II of the Envelope Protein." *mBio*, 4(6):e00873-00813 (2013).

Villar, et al., "Efficacy of a Tetravalent Dengue Vaccine in Children in Latin America." *N Engl J Med*, 372(2):113-123 (2015).

Dejnirattisai, et al., Dengue virus sero-cross-reactivity drives antibody-dependent enhancement of infection with zika virus. Nat Immunol. 7(9): 1102-8. 2016.

Laoprasopwattana, et al., "Dengue Virus (DV) enhancing antibody activity in preillness plasma does not predict subsequent disease severity or viremia in secondary DV infection." J Infect Dis. 192(3):510-9. 2005.

Libraty, et al., "A prospective nested case-control study of Dengue in infants: rethinking and refining the antibody-dependent enhancement dengue hemorrhagic fever model." PLoS Med. 6(10):e1000171. 2009.

* cited by examiner

SEQUENCE LISTING

<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Arg Cys Pro Thr Gln Gly Glu
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Gly Trp Gly Asn Gly Cys Gly Leu Phe Gly
1               5                   10

<210> SEQ ID NO 3
<211> LENGTH: 23
<212> TYPE: PRT
<213> ORGANISM: Artificial Sequence
<220> FEATURE:
<223> OTHER INFORMATION: Synthetic

<400> SEQUENCE: 3

Gly Trp Gly Asn Gly Cys Gly Leu Phe Gly Gly Gly Gly Gly Gly
1               5                   10                  15

Arg Cys Pro Thr Gln Gly Glu
            20

<210> SEQ ID NO 4
<211> LENGTH: 23
<212> TYPE: PRT
<213> ORGANISM: Artificial Sequence
<220> FEATURE:
<223> OTHER INFORMATION: Synthetic

<400> SEQUENCE: 4

Gly Trp Gly Asn Gly Cys Gly Leu Phe Gly Gly Gly Gly Gly Gly
1               5                   10                  15

Arg Cys Pro Thr Gln Gly Glu
            20

<210> SEQ ID NO 5
<211> LENGTH: 14
<212> TYPE: PRT
<213> ORGANISM: Artificial Sequence
<220> FEATURE:
<223> OTHER INFORMATION: Synthetic

<400> SEQUENCE: 5

Gly Gly Gly Gly Gly Gly Gly Arg Cys Pro Thr Gln Gly Glu
1               5                   10

BIVALENT DENGUE/HEPATITIS B VACCINES

STATEMENT OF GOVERNMENTAL SUPPORT

This invention was made with government support under Grant number R01AI091820 awarded by the National Institutes of Health and the National Institute of Allergy and Infectious Diseases. The Government has certain rights in the invention.

A Sequence Listing has been submitted in an ASCII text file named "18991.txt" created on Jan. 13, 2021, consisting of 1,497 bytes, the entire content of which is herein incorporated by reference.

FIELD OF THE INVENTION

The present invention relates to the construction of, and immunization of mammals with, viral vaccines. In particular, bivalent vaccines that are capable of providing simultaneous virus infection protection for two or more different viruses simultaneously are disclosed. Furthermore, the bivalent vaccines contemplated herein are contemplated as being effective in a neonatal mammal. One such bivalent viral vaccine comprises two antigenic epitopes against the dengue viruses and at least one antigenic epitope against the hepatitis B virus. Immunization cross-reactivity may also provide infection protection against other viruses as well.

BACKGROUND

Dengue is believed to be a prevalent arthropod-borne viral illness in humans with half of the world's population at risk. For example, the global burden of symptomatic dengue has been reported to be on the order of 100 million cases/year. Bhatt et al., "The global distribution and burden of dengue" *Nature* 2013; 496(7446):504-7. The dengue viruses (DENVs) are single-stranded, positive-sense, RNA-containing enveloped viruses belonging to the Flavivirus genus within the Flaviviridae family. Henchal et al., "The dengue viruses" *Clin Microbial Rev.* 1990; 3(4):376-96. Four serotypes of DENVs (DENVs 1-4) are generally known. Developing a DENV vaccine is the primary preventive goal for disease control. In order to prevent serial infections with more than one DENV serotype, vaccination strategies have been examining products directed against all four (4) DENV serotypes simultaneously There is an ongoing need for an improved dengue vaccine product. What is needed in the art is a dengue vaccine product capable of inducing high and long-lasting levels of broadly-neutralizing antibodies to DENVs 1-4 with a low antibody enhancing activity.

SUMMARY OF THE INVENTION

The present invention relates to the construction of, and immunization of mammals with, viral vaccines. In particular, bivalent vaccines that are capable of providing simultaneous protection against virus infection with two or more different viruses. Furthermore, the bivalent vaccines contemplated herein are contemplated as being effective in a neonatal mammal. One such bivalent viral vaccine comprises two antigenic epitopes against the dengue viruses and at least one antigenic epitope against the hepatitis B virus. Immunization cross-reactivity may also provide infection protection against other viruses as well.

In one embodiment, the present invention contemplates a vaccine peptide comprising a first dengue virus antigenic epitope, a spacer peptide and a second dengue virus antigenic epitope, wherein said spacer peptide is attached to said first dengue virus antigenic epitope and said second dengue virus antigenic epitope. In one embodiment, the spacer peptide comprises a plurality of glycine residues. In one embodiment, the plurality of glycine residues comprises at least six glycine residues. In one embodiment, the bivalent vaccine peptide further comprises a crosslinker. In one embodiment, the bivalent vaccine peptide further comprises a hepatitis B virus epitope conjugated to said second dengue virus antigenic epitope with a crosslinker. In one embodiment, the bivalent vaccine peptide further comprises a hepatitis B virus epitope attached to said first dengue antigenic epitope with a crosslinker. In one embodiment, the vaccine peptide further comprises a first hepatitis B virus epitope conjugated to said first dengue virus antigenic epitope and a second hepatitis B virus epitope conjugated to said second dengue virus antigenic epitope with a crosslinker. In one embodiment, said first dengue virus antigenic epitope is SEQ ID NO:1. In one embodiment, said second dengue virus antigenic epitope is SEQ ID NO:2. In one embodiment, said hepatitis B virus epitope is rHepBsAg. In one embodiment, the bivalent vaccine peptide is SEQ ID NO:4. In one embodiment, the crosslinker comprises a carboxyl reactive group and an amine reactive group. In one embodiment, the crosslinker comprises a sulfydryl reactive group. In one embodiment, the crosslinker comprises a heterobifunctional crosslinker. In one embodiment, the heterobifunctional crosslinker comprises an amine reactive group and a carboxyl reactive group or a sulfhydryl reactive group.

In one embodiment, the present invention contemplates a method, comprising: a) providing; i) a mammal in need of a broad viral spectrum vaccination; and ii) a bivalent vaccine peptide comprising a first dengue virus antigenic epitope, a spacer peptide and a second dengue virus antigenic epitope, wherein said spacer peptide is attached to said first dengue virus antigenic epitope and said second dengue virus antigenic epitope; and b) immunizing said mammal with said bivalent vaccine peptide under conditions such that: i) protective levels of neutralizing antibodies to said first dengue virus antigenic epitope and neutralizing antibodies to said second dengue virus antigenic epitope are produced; and ii) clinically ineffective levels of enhancing antibodies to said first dengue virus antigenic epitope monoclonal antibodies and antibodies to said second dengue virus antigenic epitope antibodies are produced. In one embodiment, the spacer peptide comprises a plurality of glycine residues. In one embodiment, the plurality of glycine residues comprises at least six glycine residues. In one embodiment, the bivalent vaccine peptide further comprises a crosslinker. In one embodiment, the bivalent vaccine peptide further comprises a hepatitis B virus epitope conjugated to said second dengue virus antigenic epitope with a crosslinker. In one embodiment, the method further comprises immunizing said mammal with said hepatitis B virus epitope under conditions such that protective levels of antibodies to said hepatitis B virus epitope are produced. In one embodiment, said mammal is a neonatal mammal. In one embodiment, said mammal is an adolescent mammal. In one embodiment, said mammal is an adult mammal. In one embodiment, the bivalent vaccine peptide further comprises a hepatitis B virus epitope conjugated to said second dengue virus antigenic epitope with a crosslinker. In one embodiment, the bivalent vaccine peptide further comprises a hepatitis B virus epitope conjugated to said first dengue virus antigenic epitope with a crosslinker. In one embodiment, the bivalent vaccine peptide further comprises a first hepatitis B virus epitope conjugated to said first dengue virus antigenic epitope and a second hepatitis B virus epitope conjugated to said second dengue virus antigenic epitope with a crosslinker. In one embodiment, said first dengue virus antigenic epitope is SEQ ID NO:1. In one embodiment, said second dengue virus antigenic epitope is SEQ ID NO:2. In one embodiment, said hepatitis B virus epitope is rHepBsAg. In one embodiment, the bivalent vaccine peptide is SEQ ID NO:4. In one embodiment, the method further comprises immunizing said mammal with SEQ ID NO:4. In one embodiment, the crosslinker comprises an amine reactive group. In one embodiment, the crosslinker comprises a sulfhydryl reactive group. In one embodiment, the crosslinker comprises a heterobifunctional crosslinker. In one embodiment, the heterobifunctional crosslinker comprises an amine reactive group and a carboxyl reactive group or a sulfhydryl reactive group.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" or "approximately" as used herein, in the context of any of any assay measurements refers to +/−5% of a given measurement.

The term, "bivalent" as used herein, refers to a single peptide having two distinct antigenic sites derived from proteins of the same virus (e.g., a dengue virus). Such antigenic sites may be derived from peptide sequences of the same, or different, proteins and/or species. For example, a bivalent vaccine peptide may have a first antigenic site derived from a first viral protein (e.g., for example, a first dengue viral protein) and a second viral protein (e.g., for example, a second dengue viral protein).

The term, "vaccine peptide" as used herein, refers to an amino acid sequence comprising at least one antigenic region that is capable of producing neutralizing antibodies when used to immunize a mammal as described herein.

The term "antigenic epitope" as used herein, refers to a region of an amino acid sequence that is capable of inducing the production of neutralizing antibodies subsequent to an interaction with a mammalian lymphocyte cell (e.g., a T lymphocyte).

The term "spacer peptide" as used herein, refers to a non-immunogenic amino acid sequence located within a vaccine peptide that provides a spatial separation between a first antigenic epitope and a second antigenic epitope. For example, the spacer peptide may comprise a plurality of glycine amino acid residues (e.g., approximately six (6) glycine residues).

The term "crosslinker" as used herein, refers to a polymer of non-immunogenic repeating monomers that conjugates a vaccine peptide comprising an antigenic epitope from a first virus to a vaccine peptide comprising an antigenic epitope from a second virus. For example, a crosslinker may conjugate a dengue vaccine peptide to a hepatitis virus-like particle.

The term "heterobifunctional" as used herein, refers to a molecule having at least two different chemical reactive groups. For example, a hetereobifunctional molecule may have an amine reactive group and a carboxyl or sulfhydryl reactive group.

The term "amine reactive group" as used herein, refers to any chemical moiety capable of forming covalent bonds with an amine group.

The term "carboxyl reactive group" as used herein, refers to any chemical moiety capable of forming covalent bonds with an carboxyl group. The term "sulfhydryl reactive group" as used herein, refers to any chemical moiety capable of forming covalent bonds with a sulfhydryl group.

The term "broad spectrum viral vaccination" as used herein, refers to an immunization method that uses a vaccine that produces neutralizing antibodies to more than one viral antigen simultaneously. For example, a broad spectrum viral vaccination may produce neutralizing antibodies to more than one antigenic epitope from the same or different proteins of the same virus, proteins of different viruses or a combination thereof.

The term "viral-infection protective levels" as used herein, refers to a level of production of neutralizing antibodies capable of reducing and/or preventing a viral infection.

The term "clinically ineffective levels" as used herein, refers to a level of production of enhancing antibodies that do not contribute to propagating a viral infection.

The term "neutralizing antibodies" as used herein, refers to an antibody type that adheres to a virus particle and reduces and/or prevents infection of a host.

The term "enhancing antibodies" as used herein, refers to an antibody type that adheres to a virus particle and facilitates infection of a host.

The term "effective amount" as used herein, refers to a particular amount of a vaccine that achieves a clinically beneficial result (i.e., for example, a reduction or prevention of a viral infection). Toxicity and therapeutic efficacy of such vaccines can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "attached" as used herein, refers to any interaction between two molecules which may be of the same or different chemical class. Attachment may be reversible or irreversible. Such attachment includes, but is not limited to, covalent bonding, ionic bonding, Van der Waals forces or friction, and the like.

The term "conjugated" as used herein, refers to a covalent bonding of two molecules which are of different chemical classes.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "test compound" as used herein, refers to any compound or molecule considered a candidate as an inhibitory compound.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "polypeptide", refers to any of various amides that are derived from two or more amino acids by combination of the amino group of one acid with the carboxyl group of another and are usually obtained by partial hydrolysis of proteins. In general, a peptide comprises amino acids having an order of magnitude with the tens or larger.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that all trace impurities have been removed.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The terms "amino acid sequence" and "polypeptide sequence" as used herein, are interchangeable and to refer to a sequence of amino acids.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "immunologically active" defines the capability of a natural, recombinant or synthetic peptide, or any oligopeptide thereof, to induce a specific immune response in appropriate animals or cells and/or to bind with specific antibodies.

The term "antigenic determinant" as used herein refers to that portion of a molecule that is recognized by a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "immunogen," "antigen," "immunogenic" and "antigenic" refer to any substance capable of generating antibodies when introduced into an animal. By definition, an immunogen must contain at least one epitope (the specific biochemical unit capable of causing an immune response), and generally contains many more. Proteins are most frequently used as immunogens, but lipid and nucleic acid moieties complexed with proteins may also act as immunogens. The latter complexes are often useful when smaller molecules with few epitopes do not stimulate a satisfactory immune response by themselves.

BRIEF DESCRIPTION OF THE FIGURES

FIG. 2 presents exemplary illustrations of experimental structures of
FIG. 2A: DENV2
FIG. 2B: DENV3 envelope proteins. (cgl.ucsf.edu/chimera).

II. Bivalent Epitope Dengue Vaccine Compositions

In one embodiment, the present invention contemplates a bivalent dengue vaccine configured to induce high and long-lasting levels of broadly neutralizing antibodies against DENVs 1-4 with low anti-DENV antibody enhancing activity. In one embodiment, the vaccine comprises a synthetic peptide that contains two (2) conserved envelope protein conformational epitopes adjacent to, and in, the fusion loop. In one embodiment, the dengue vaccine is linked to the hepatitis B virus surface antigen (e.g., rHepBsAg) virus-like particles (VLPs) (the hepatitis B vaccine) as a carrier. In one embodiment, the hepatitis B virus surface antigen VLP is a yeast cell-derived recombinant hepatitis B virus surface antigen VLP. Although it is not necessary to understand the mechanism of an invention, it is believed that a synthetic peptide that contains two (2) conserved envelope protein conformational epitopes adjacent to, and in, the fusion loop, and recognized by anti-DENVs 1-4 broadly neutralizing antibodies, can be linked to yeast cell-derived recombinant hepatitis B virus surface antigen (rHepBsAg) virus-like particles (VLPs) (the hepatitis B vaccine) as the carrier.

A. Development and Clinical Strategy

There are several advantages to utilizing rHepBsAg as a carrier protein linked to a dengue vaccine. For example, a yeast cell-derived rHepBsAg (the hepatitis B vaccine) has been clinically very effective as an immunogenic vaccine that can be given starting in the neonatal period. Further, a hepatitis B vaccine's immunogenicity likely derives from an ability of rHepBsAg to self-assemble into VLPs, and the presence of yeast-derived lipids serve as an adjuvant in the vaccine, thereby providing additive efficacy. The hepatitis B vaccine has been incorporated into the World Health Organization (WHO) Expanded Programme on Immunization (EPI) throughout the world. Consequently, a synthetic dengue peptide vaccine that induces broadly neutralizing antibodies against all 4 DENV serotypes with low anti-DENVs 1-4 antibody enhancing activity, and conjugated to the hepatitis B vaccine, would take advantage of the hepatitis B vaccine's immunogenicity and allow a single vaccine series to protect against both hepatitis B and dengue starting at birth.

Although it is not necessary to understand the mechanism of an invention, it is believed that a balance between anti-DENV neutralizing antibodies and anti-DENV enhancing antibody activities depends on several factors: i) the targeted epitope(s); ii) the antibody titer; iii) the mix of immature and mature virus particles; and iv) the infecting cell type. It is further believed that essentially all anti-DENV antibodies with neutralizing activity have also been found to have varying degrees of activity that enhance DENV infection in Fcγ receptor-bearing cells, and usually at lower antibody titers.

In some embodiments, the present invention contemplates a vaccination method having a high likelihood of generating antibody responses with high neutralizing capability (e.g., viral-infection protection) and low enhancing activities (e.g., clinically ineffective infection enhancement) to DENVs 1-4. In one embodiment, the method comprises a synthetic bivalent dengue peptide vaccine generating a neutralizing antibody titer to more than one of the conserved conformational epitopes involved in the fusion process of the DENV envelope glycoprotein.

It has been recently reported that a passive immunization with a broadly neutralizing human monoclonal antibody directed against the DENV envelope protein fusion loop protected against viremia in DENV2-challenged rhesus macaques. Simmons et al., "Antibody Prophylaxis Against Dengue Virus 2 Infection in Non-Human Primates" Am J Trop Med Hyg. (2016) 95(5):1148-56. In one embodiment, conjugation of a synthetic dengue peptide vaccine linked to a rHepBsAg VLP (the hepatitis B vaccine) induces high and long-lasting antibody titers, and thereby minimizes the production of potential antibodies that enhance infection activity. In one embodiment, a synthetic dengue peptide vaccine lacks DENV prM protein epitopes (e.g., derived from immature virus particles), which also contributes to the minimization of potential antibody enhancing activity.

In one embodiment, the present invention contemplates a method comprising: i) immunizing a mammal with a bivalent dengue vaccine peptide conjugated to a hepatitis B vaccine; ii) immunizing a mammal with a hepatitis B vaccine, and iii) immunizing a mammal with the dengue vaccine peptide. Although it is not necessary to understand the mechanism of an invention, it is believed that differences between these two immunization vaccines will demonstrate that the conjugated vaccine has high anti-DENV's 1-4 neutralizing antibody activity, low anti-DENV's 1-4 enhancing antibody activity, and an equivalent anti-HepBsAg antibody titer.

B. Vaccine Construction

Adjacent to a fusion loop of a DENV envelope protein, an epitope in the bc loop was found to be recognized by a potent broadly neutralizing human monoclonal antibody (e.g., mAb 1C19). Smith et al., "The potent and broadly neutralizing human dengue virus-specific monoclonal antibody 1C19 reveals a unique cross-reactive epitope on the bc loop of domain II of the envelope protein" MBio. (2013) 4(6): e00873-13. This seven (7) amino acid peptide sequence (RCPTQGE: SEQ ID NO:1) resides in the bc loop and was found to be conserved in 5,495 DENV envelope protein sequences encompassing all four (4) DENV serotypes (ViPR database, viprbrc.org). Similarly, a conserved ten (10) amino acid peptide sequence (GWGNGCGLFG: SEQ ID NO:2) was located in a fusion loop of DENV envelope proteins. This ten amino acid sequence was found to contain active binding residues for several broadly neutralizing human monoclonal antibodies. Costin et al., "Mechanistic study of broadly neutralizing human monoclonal antibodies against dengue virus that target the fusion loop" J Virol. 2013) 87(1):52-66. This ten amino acid sequence peptide was found to be conserved in 10,029 DENV envelope protein sequences encompassing all four (4) DENV serotypes (ViPR database, viprbrc.org). Neither SEQ ID NO:1 nor SEQ ID NO:2 are present in a HepBsAg protein (e.g., the adw subtype).

Figure 1:
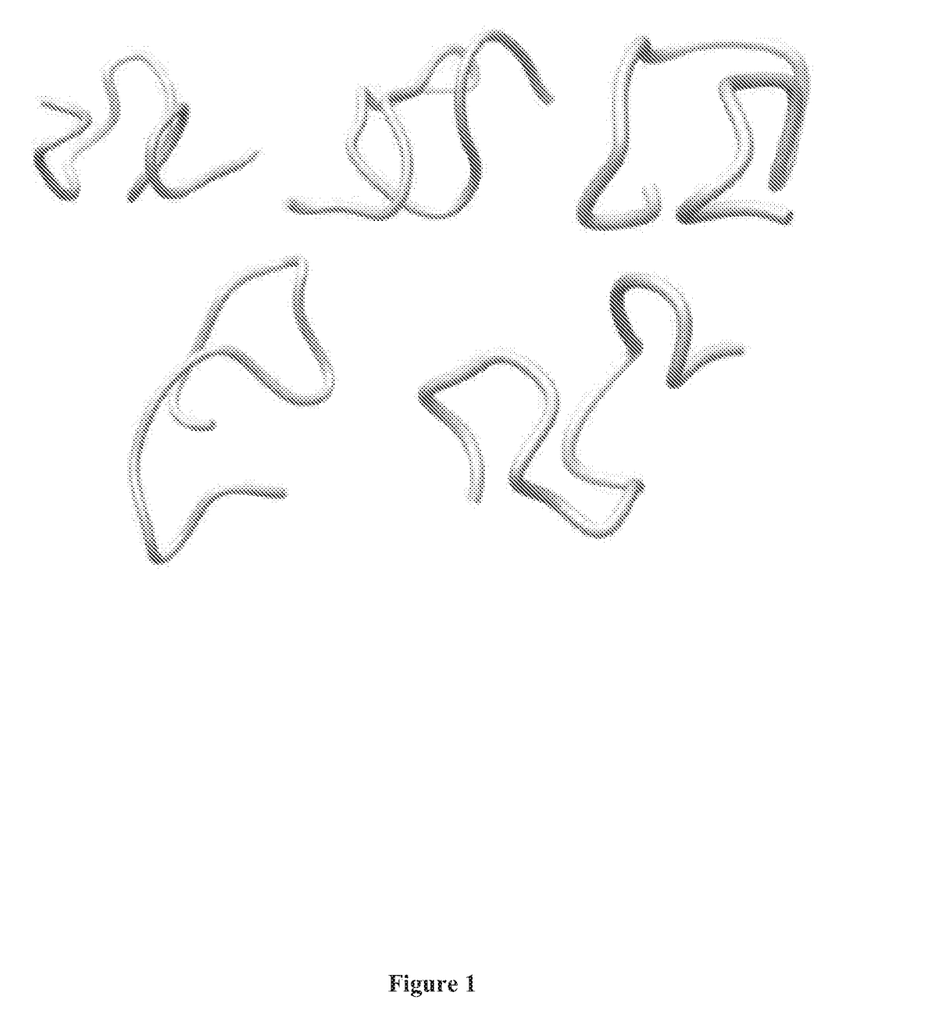
FIG. 1 presents exemplary illustrations of predicted 3D structures (models 1-5) of the peptide GWGNGCGLFG-GGGGGG-RCPTQGE (SEQ ID NO:3). (bioserv.rpbs.univ-paris-diderot.fr/services/PEP-FOLD/).
Figure 2A:
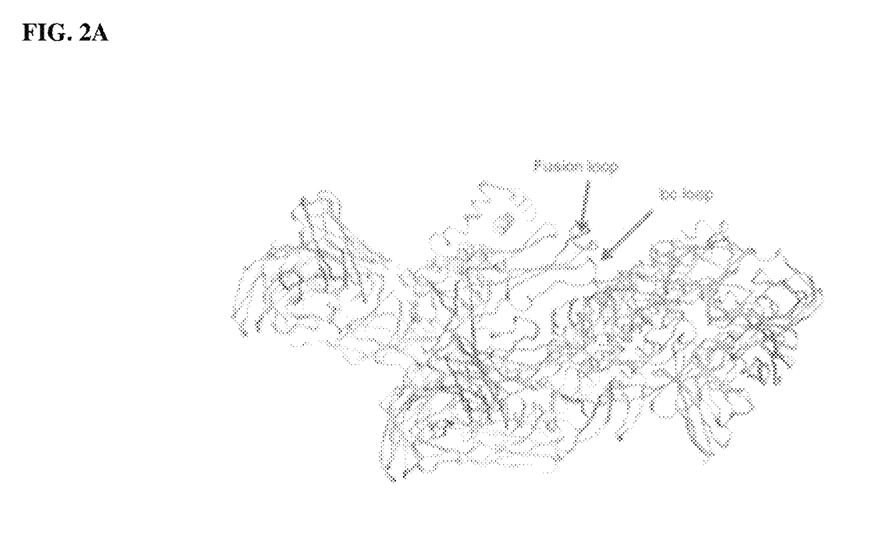
Figure 2B:
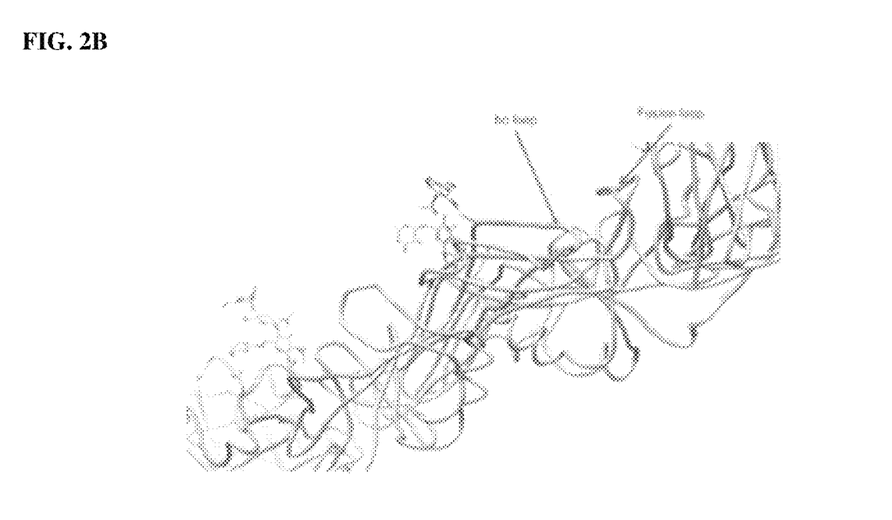

In one embodiment, the present invention contemplates a 23mer synthetic peptide containing SEQ ID NO:1 and SEQ ID NO:2 are attached with a spacer protein that may comprise a plurality of glycine residues. In one embodiment, the 23mer synthetic peptide comprises six (6) glycine residue. In one embodiment, the 23mer synthetic peptide has the amino acid sequence of GWGNGCGLFGGGGGG-GRCPTQGE (SEQ ID NO:3; the first and second conserved DENV epitopes are italicized for emphasis). In one embodiment, SEQ ID NO:1 is derived from a DENV envelope protein. In one embodiment, SEQ ID NO:2 is derived from a DENV envelope protein. Although it is not necessary to understand the mechanism of an invention, it is believed that a glycine spacer peptide placed between the two conserved DENV epitopes allows the steric flexibility for different antibodies/B-cell receptors to bind to each of the respective epitopes simultaneously. In fact, predicted 3D structures of this synthetic peptide show open loops encompassing both neutralizing antibody epitopes. See, FIG. 1. Furthermore, structures of the DENV2&3 envelope proteins demonstrate that these two conserved epitopes, recognized by anti-DENVs 1-4 broadly neutralizing antibodies, also form open loops. ViPR database, viprbrc.org; and FIG. 2. In one embodiment, the synthetic bivalent dengue vaccine peptide GWGNGCGLFG-GGGGGG-RCPTQGE (SEQ ID NO:3) comprises at least two cysteine residues, for example, at amino acid residues six (6) and eighteen (18). Although it is not necessary to understand the mechanism of an invention, it is believed that these two cysteine residues do not form a disulfide bond. Ensemble-based Disulfide Bonding Connectivity Pattern Prediction Server, biomedical.ctust.edu.tw/edbcp.

Although it is not necessary to understand the mechanism of an invention, it is believed that a conjugation of GWGNGCGLFG-GGGGGG-RCPTQGE (SEQ ID NO:3) with rHepBsAg maximizes the probability that a carboxyl reactive end of a crosslinker will attach to carboxyl groups of a rHepBsAg protein An et al., "Preparation and testing of a *Haemophilus influenzae* Type b/Hepatitis B surface antigen conjugate vaccine" *Vaccine* (2015) 33(13):1614-9. and that an amine reactive end of a crosslinker will attach to an N-terminus of SEQ ID NO:3. Other combinations may occur, but preliminary studies suggest that SEQ ID NO:3 is the most likely fusion protein combination. In the event a different approach is required, the peptide GWGNGCGLFG-GGGGGG-RCPTQGE (SEQ ID NO:3) could be attached to a crosslinker using a carboxyl group on, for example, a C-terminal glutamate residue or by using a sulfhydryl group on a cysteine residue. Alternatively, sulfhydryl groups are available on reduced cysteine residues on the HepBsAg protein could also be involved in crosslinker conjugation.

In one embodiment, the present invention contemplates a bivalent dengue vaccine comprising at least two conserved epitopes recognized by anti-DENVs 1-4 broadly neutralizing antibodies and a crosslinker attaching the bivalent dengue vaccine to a yeast-cell derived rHepBsAg. In one embodiment, at least two conserved epitopes are conformational epitopes. In one embodiment, the bivalent dengue vaccine is GWGNGCGLFG-GGGGGG-RCPTQGE (SEQ ID NO: 3). In one embodiment, the yeast-cell derived rHepBsAg is the adw subtype. In one embodiment, the crosslinker is non-immunogenic. In one embodiment, the crosslinker is a heterobifunctional crosslinker. In one embodiment, the crosslinker comprises an amine reactive group. In one embodiment, the crosslinker comprises a carboxyl reactive group. In one embodiment, the crosslinker comprises an amine reactive group and a carboxyl reactive group. In one embodiment, the bivalent dengue/rHepBsAg vaccine is rHepBsAg-GWGNGCGLFG-GGGGGG-RCPTQGE (SEQ ID NO:4). Although it is not necessary to understand the mechanism of an invention, it is believed that a crosslinker attaches a synthetic dengue vaccine peptide to a rHepBsAg in such a configuration to allow anti-HepBsAg antibodies to develop. If a spacer is required in order to generate anti HepBsAg IgG antibodies, alternative strategies can use a homobifunctional crosslinker containing 9 repeating units of polyethylene glycol ((PEG)9) (spacer arm 35.8 angstroms) with either two amine reactive ends or two sulfhydryl reactive ends (for conjugation to reduced cysteine residues in the rHepBsAg protein and the 23mer synthetic peptide).

It was previously reported that a crosslinker facilitated the generation of anti-HepBsAg antibodies in immunized mice when conjugating a hapten to rHepBsAg. An et al., "Preparation and testing of a *Haemophilus Influenzae* Type b/Hepatitis B surface antigen conjugate vaccine" Vaccine (2015) 33(13):1614-9.

EXPERIMENTAL

Example I

Construction of A Bivalent Dengue/rHepBsAg Vaccine

To generate rHepBsAg-GWGNGCGLFGGGGGG-GRCPTQGE (SEQ ID NO: 4)

1. Equilibrate all solutions to room temperature before using.
2. Make a solution of EDC (1-ethyl-3-(3-dimethylaminopropyl)carbodiimide hydrochloride) 5 mg/ml in 100 mM MES (2-(N-morpholino)ethanesulfonic acid) activation buffer pH 5.5-5.7.
3. Add 100 mM MES activation buffer, pH 5.5-5.7, to the HepBsAg vial (50 µg) (2.1×10−3 µmoles) to bring the final volume to 100 µl (2×10−5 µM).
4. Add 1 µl of EDC solution to 100 µl HepBsAg solution.
5. Make a solution of sulfo-NHS 15 mg/ml in 100 mM MES activation buffer pH 5.5-5.7
6. Add 1 µl of the sulfo-NHS solution to the HepBsAg/EDC solution.
7. Incubate (mix well)×15 minutes at room temp.
8. Dialyze against PBS pH 7.2 (20 kDa membrane)×1 hour at room temp.
9. Increase the pH of the dialysate to pH 8 with NaOH (do this after making the peptide solutions below).
10. Add 25×10−3 µmoles of the 23mer synthetic peptide to the HepBsAg/EDC/sulfo-NHS (N-hydroxysulfosuccinimide) solution pH 8. (use solutions of the peptide in PBS pH 8 in order to do this).
11. Mix well and incubate ×2 hours at room temp.
12. Dialyze against PBS pH 7.2 overnight at 4 deg C.

Example II

Confirmation of rHepBsAg-GWGNGCGLFGGGGGGGRCPTQGE (SEQ ID NO:4) VLP Generation This example confirms the generation of rHepBsAg-GWGNGCGLF-GGGGGGGRCPTQGE (SEQ ID NO:4) VLPs.

In order to remove any remaining excess free synthetic peptide, rHepBsAg-GWGNGCGLFG-GGGGGG-RCPTQGE (SEQ ID NO:4) VLPs were desalted, run on a SDS-PAGE gel, and the VLP band was excised for proteomic analysis. After chymotrypsin digestion, digest products from HepBsAg (adw subtype) and the synthetic peptide digest product GGGGGGGRCPTQGE (SEQ ID NO:5) were detected by MALDI-TOF mass spectrometry.

Example III

Immunization of a Mammal With rHepBsAg-GWGNGCGLFGGGGGGGRCPTQGE (SEQ ID NO:4) VLP This example demonstrates the immunization of female Balb/c mice with rHepBsAg-GWGNGCGLFGGGGGG-GRCPTQGE (SEQ ID NO:4). See, FIG. 3.

Serum anti-DENVs 1-4 neutralizing antibody titers were measured using a U937/DC-SIGN flow cytometry based neutralization assay and serum anti-HepBsAg IgG levels using an ELISA. de Alwis et al., "Measuring antibody neutralization of dengue virus (DENY) using a flow cytometry-based technique" Methods Mol Biol. (2014) 1138:27-39.

Figure 5:
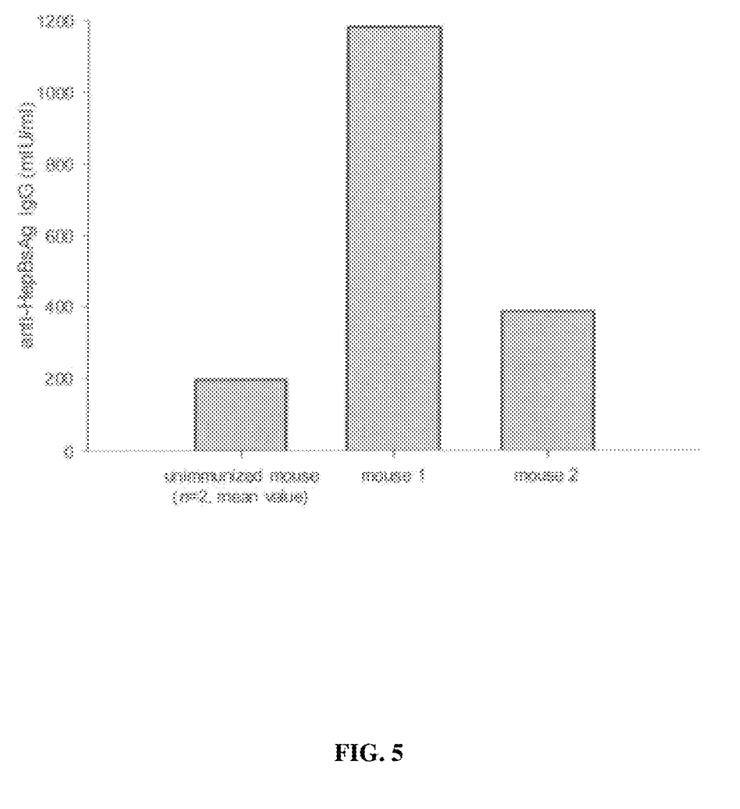

The data show that an active immunization with SEQ ID NO:4 produced a potent (e.g, demonstrated by a high avidity) anti-DENV 1-4 neutralizing antibodies in Balb/c mice. See, FIGS. 4A-4D. The Hill slopes of the sigmoid neutralization curves shown in FIG. 4 reflect the avidities of the vaccine-induced neutralizing antibodies. The $EC_{50}$'s reflect the serum neutralizing antibody titers. The $EC_{50}$ is a function of an antigen dose used in an immunization protocol and an amount of virus used in the in vitro antibody neutralization assays. There are no pre-defined correlates of protective immunity for anti-DENV neutralizing antibodies in either humans or any animal model. The data also verify that anti-HepBsAg IgG antibodies were produced in the above described immunization. See, FIG. 5.

Example IV

Figure 3:
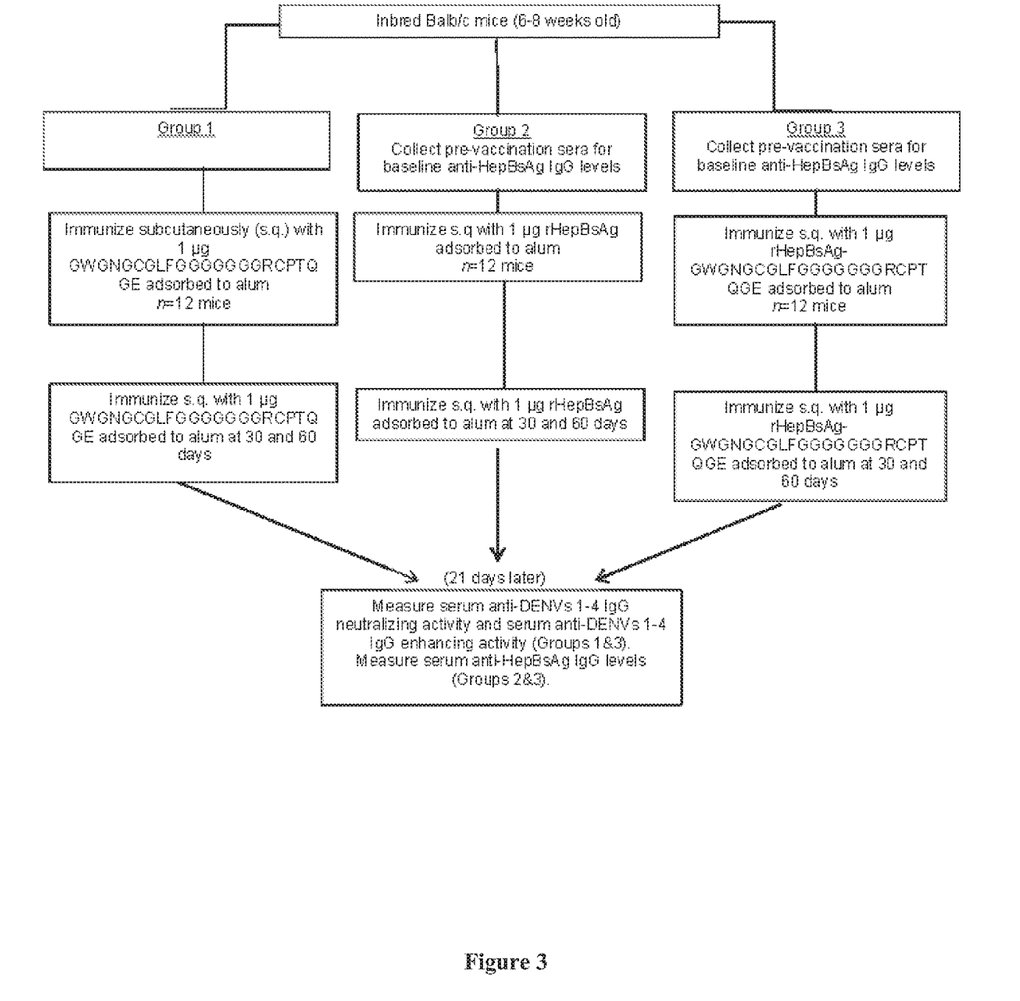
FIG. 3 presents one embodiment of a method for the mouse vaccination.
Figure 4A:
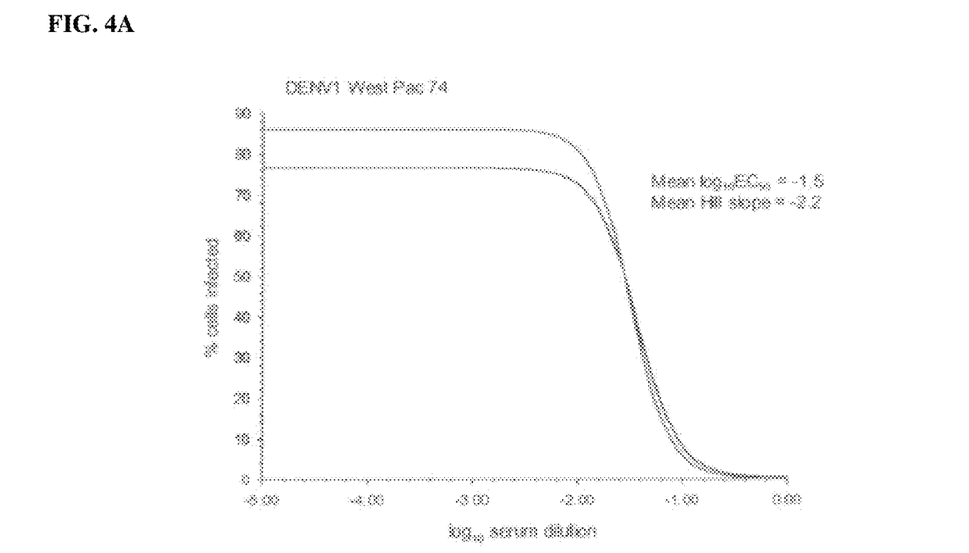
FIG. 4 presents exemplary data of serum anti-DENVs 1-4 neutralizing antibody curves in female Balb/c mice vaccinated with a bivalent dengue vaccine peptide (e.g., rHepBsAg-GWGNGCGLFG-GGGGGG-RCPTQGE; SEQ ID NO:4) using a protocol shown above in FIG. 3. Anti-DENV's 1-4 antibody neutralization assays were performed ut America" N Engl 1 Med. (2015) 372(2):113-23; and Sabchareon et al., "Protective efficacy of the recombinant, live-attenuated, CYD tetravalent dengue vaccine in Thai schoolchildren: a randomised, controlled phase 2b trial" Lancet (2012) 380(9853):1559-67. In addition, the yellow fever/dengue vaccine protocol requires three (3) injections over a period of twelve (12) months and is only approved for older children. Another tetravalent live attenuated dengue vaccine product (e.g., by a deletion in the DENV 3' UTR region) is beginning Phase III clinical trials. Other dengue vaccine products that are still in pre-clinical phases include an adjuvanted recombinant envelope protein vaccine, an adjuvanted purified inactivated virus vaccine, and a plasmid DNA vaccine.
Figure 4B:
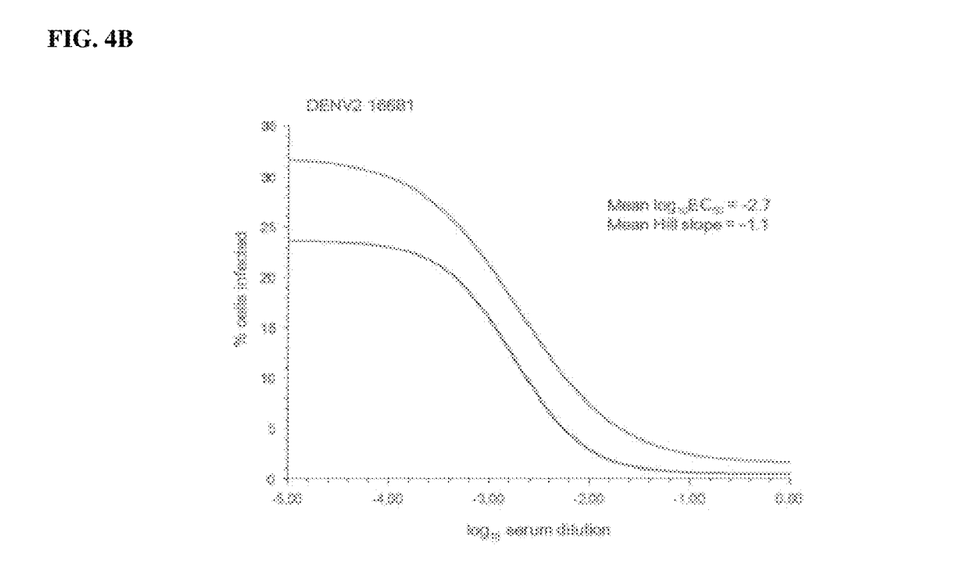
Figure 4C:
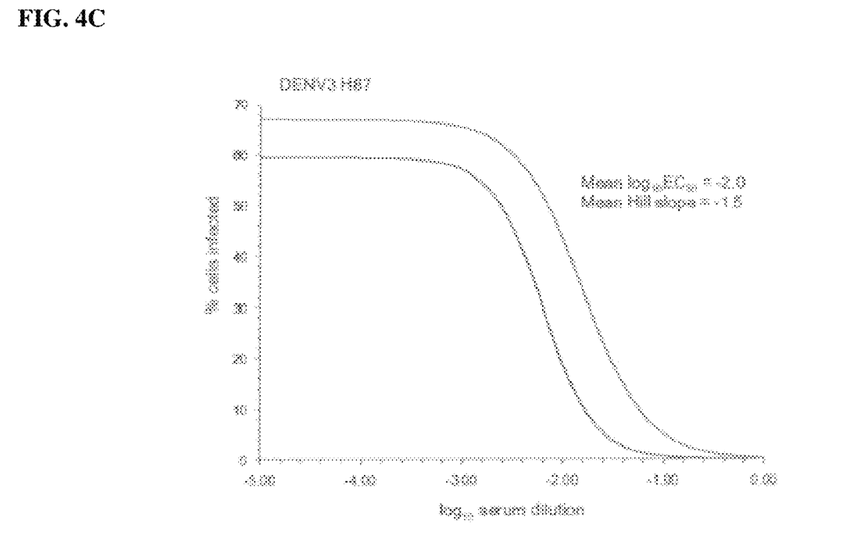
Figure 4D:
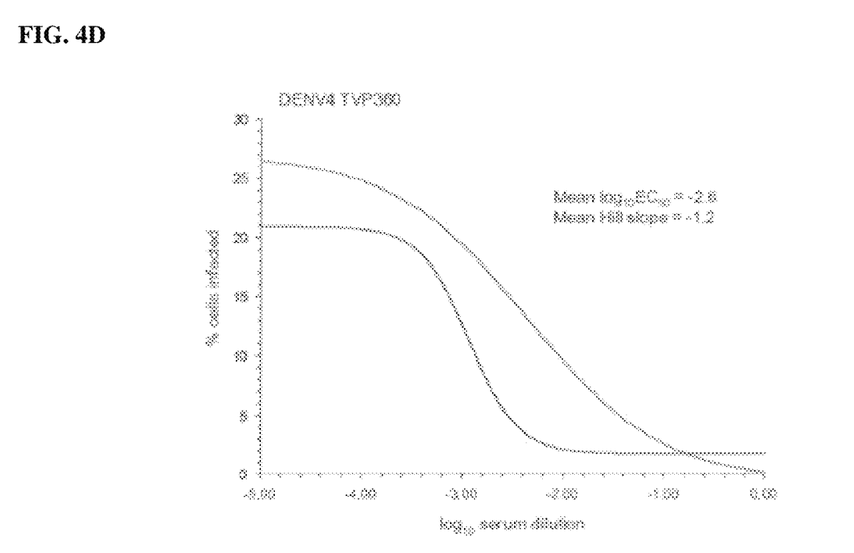

Comparative Analysis of Immunization of a Mammal with rHepBsAg-GWGNGCGLFGGGGGGGRCPTQGE (SEQ ID NO:4) VLP with rHepBsAg or GWGNGCGLFGGGGGGGRCPTQGE (SEQ ID NO:4) Immunization Alone Inbred Balb/c mice will be divided into three groups (n=12 mice/group, n=6 female and n=6 male). One group will be immunized subcutaneously (s.q.) with 1 µg of the 23mer synthetic peptide GWGNGCGLFGGGGGG-GRCPTQGE adsorbed to alum and boosted at 30 and 60 days (group 1). The second group will be immunized s.q. with 1 µg yeast cell derived rHepBsAg VLPs adsorbed to alum and boosted at 30 and 60 days (group 2). The third group will be immunized s.q. with 1 µg rHepBsAg GWGNGCGLFGGGGGGGRCPTQGE adsorbed to alum and boosted at 30 and 60 days (group 3). 21 days after the last booster vaccination, the mice will be sacrificed and sera collected for the measurement of anti-DENVs 1-4 antibody neutralizing activity and anti DENVs 1-4 antibody enhancing activity (groups 1&3), and anti-HepBsAg IgG levels (groups 2&3). The flowchart for the vaccination protocol is shown in FIG. 3. Balb/c is the inbred mouse strain commonly used to examine hepatitis B vaccine immunogenicity. There is no immunocompetent inbred mouse strain that provides an animal model for DENV infection. However, anti DENV neutralizing antibody activity can be measured in Balb/c mice.

Serum anti HepBsAg IgG levels will be measured by ELISA; serum anti DENVs 1-4 neutralizing antibody assays will be performed using U937/DC-SIGN cells in a flow cytometry based method; and, serum anti-DENVs 1-4 enhancing antibody assays will be performed using U937 cells in a flow cytometry based method. The flow cytometry based anti-DENV neutralizing antibody assay correlates with the current gold standard assay, the plaque reduction neutralization assay Kraus A A, Messer W, Haymore L B, de Silva A M. Comparison of plaque- and flow cytometry-based methods for measuring dengue virus neutralization. J Clin Microbiol. 2007; 45(11):3777-80. U937 is a human monocytic cell line. In previous studies, mouse antibodies (IgG2a subclass) have been able to enhance DENY infection in U937 cells. The following prototypical DENV strains will be used in the antibody neutralization and enhancement assays: DENV1 West Pacific 74, DENV2 16681, DENV3 H87, and DENV4 TVP360.

In preliminary studies, active immunization with the subunit dengue vaccine product produced potent (high avidity) anti DENVs 1-4 neutralizing antibodies and anti-HepBsAg IgG in two Balb/c mice. It is anticipated that active immunization with rHepBsAg-GWGNGCGLFG-GGGGGG-RCPTQGE (SEQ ID NO:4) in the Balb/c mice will produce high serum titers of anti-HepBsAg IgG (equivalent to rHepBsAg VLP (hepatitis B vaccine) immunization), along with high titers of potent anti DENVs 1-4 neutralizing antibodies and low anti DENVs 1-4 antibody enhancing activity. This example will demonstrate a conjugated bivalent vaccine product that elicits protection against dengue and hepatitis B viruses together, potentially starting at birth.

It is anticipated that active immunization with rHepBsAg-GWGNGCGLFG-GGGGGG-RCPTQGE (SEQ ID NO:4) in inbred Balb/c and outbred mice will produce high serum titers of anti-HepBsAg IgG (equivalent to rHepBsAg VLP (hepatitis B vaccine) immunization), along with high titers of potent anti-DENVs 1-4 neutralizing antibodies and low anti DENVs 1-4 antibody enhancing activity. Non-parametric statistical tests will be used to compare antibody titers between the three vaccination groups in the Balb/c mice (and within the male and female subgroups).

SUPPLEMENTAL REFERENCES

Brewoo et al., "Immunogenicity and efficacy of chimeric dengue vaccine (DENVax) formulations in interferon-deficient AG129 mice" Vaccine (2012) 30(8):1513-20.

Diamond et al., "Infection of human cells by dengue virus is modulated by different cell types and viral strains" J Virol. (2000) 74(17):7814-23.

Littaua et al., "Human IgG Fc receptor II mediates antibody-dependent enhancement of dengue virus infection" J Immunol. (1990) 144(8):3183-6.

Puerta-Guardo et al., "Antibody-dependent enhancement of dengue virus infection in U937 cells requires cholesterol-rich membrane microdomains" J Gen Virol. (2010) 91(Pt 2):394-403.

Shouval et al., "Improved immunogenicity in mice of a mammalian cell-derived recombinant hepatitis B vaccine containing pre-S1 and pre-S2 antigens as compared with conventional yeast-derived vaccines" Vaccine (1994) 12(15):1453-9.

I claim:

1. A bivalent vaccine peptide comprising a first conserved dengue antigenic envelope peptide located in a fusion loop that is adjacent to a second conserved dengue antigenic envelope peptide that resides in a bc loop.

2. The bivalent vaccine peptide of claim 1, further comprising a spacer peptide that attaches said first and second conserved antigenic envelope peptides.

3. The bivalent vaccine peptide of claim 2, wherein said spacer peptide comprises a plurality of glycine residues.

4. The bivalent vaccine peptide of claim 1, further comprising a crosslinker.

5. The bivalent vaccine peptide of claim 4, further comprising a hepatitis B virus epitope conjugated to said conserved second dengue antigenic envelope peptide with said crosslinker.

6. The bivalent vaccine peptide of claim 4, further comprising a hepatitis B virus epitope attached to said first conserved dengue antigenic envelope peptide with said crosslinker.

7. The bivalent vaccine peptide of claim 4, further comprising a first hepatitis B virus epitope conjugated to said first conserved dengue antigenic envelope protein and a second hepatitis B virus epitope conjugated to said second conserved dengue antigenic envelope protein with said crosslinker.

8. The bivalent vaccine peptide of claim 1, wherein said first conserved dengue antigenic envelope protein is SEQ ID NO: 1.

9. The bivalent vaccine peptide of claim 1, wherein said second conserved dengue antigenic envelope protein is SEQ ID NO:2.

10. The bivalent vaccine peptide of claim 1, wherein said bivalent vaccine peptide is SEQ ID NO:4.

11. The bivalent vaccine peptide of claim 4, wherein said crosslinker comprises an amine reactive group.

12. The bivalent vaccine peptide of claim 4, wherein said crosslinker comprises a carboxyl reactive group.

13. The bivalent vaccine peptide of claim 4, wherein crosslinker comprises a heterobifunctional crosslinker.

14. The bivalent vaccine peptide of claim 13, wherein said heterobifunctional crosslinker comprises an amine reactive group and a carboxyl reactive group.

* * * * *